United States Patent [19]
Papajohn

[11] Patent Number: 4,758,241
[45] Date of Patent: Jul. 19, 1988

[54] MENSTRUAL AND INCONTINENCE PAD

[76] Inventor: Elissa D. Papajohn, 65 Montague St., Brooklyn, N.Y. 11201

[21] Appl. No.: 63,413

[22] Filed: Jun. 18, 1987

[51] Int. Cl.⁴ .............................................. A61F 13/16
[52] U.S. Cl. ..................................... 604/387; 604/397
[58] Field of Search .................. 604/385.1, 385.2, 386, 604/387, 380, 375, 389, 390, 397, 398, 391

[56] References Cited

U.S. PATENT DOCUMENTS 3,805,790 4/1974 Kaczmarzyk et al. ............. 604/387
3,881,490 5/1975 Whitehead et al. ............ 604/380 X
4,579,556 4/1986 McFarland ....................... 604/385.1

FOREIGN PATENT DOCUMENTS 2168253 6/1986 United Kingdom ................ 604/375

Primary Examiner—John D. Yasko

[57] ABSTRACT

A sanitary napkin is formed of a plurality of vertically stacked layers comprising an underply of fluid impervious material, an intermediate ply of absorbent material, an underply of fluid impervious material and a peripheral binding ply of fluid impervious material having an inner and outer peripheral edge and defining a central opening into the body. The plies are adhered together about their outer peripheral edge and include an elastomeric member along each of the longitudinal side edges of the body, which resiliently contracts the body in the longitudinal direction drawing the body into a cup shape providing a deep compartment for retaining fluid between the underply and the intermediate ply and at the same time, raising the inner peripheral edge of the binding ply to form a continuous encircling wall against the flow of fluid from the compartment.

1 Claim, 2 Drawing Sheets

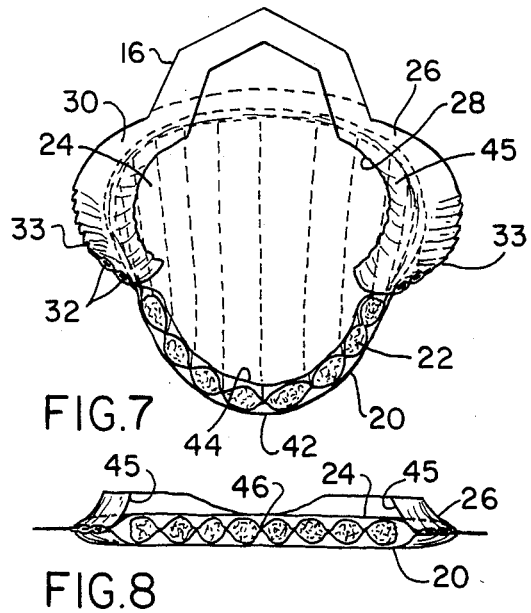
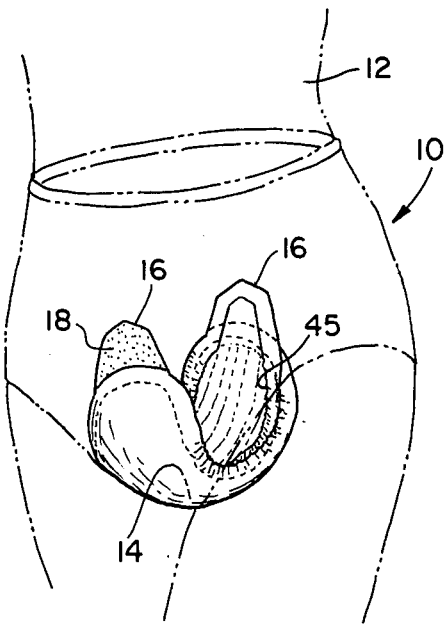
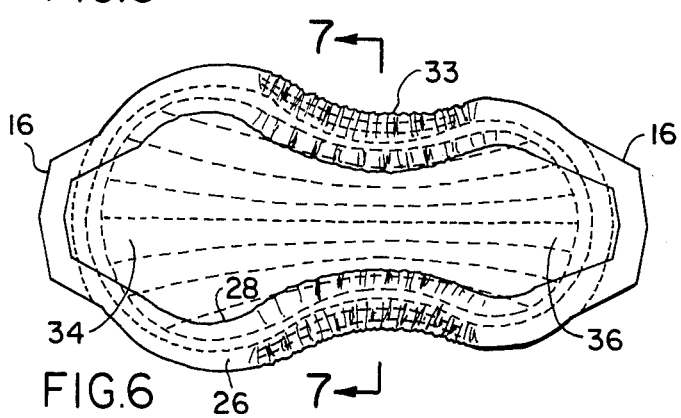
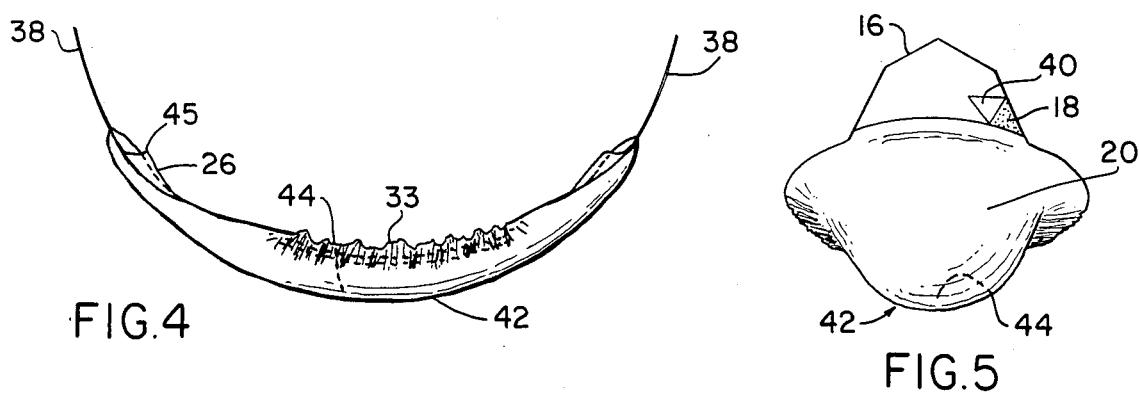

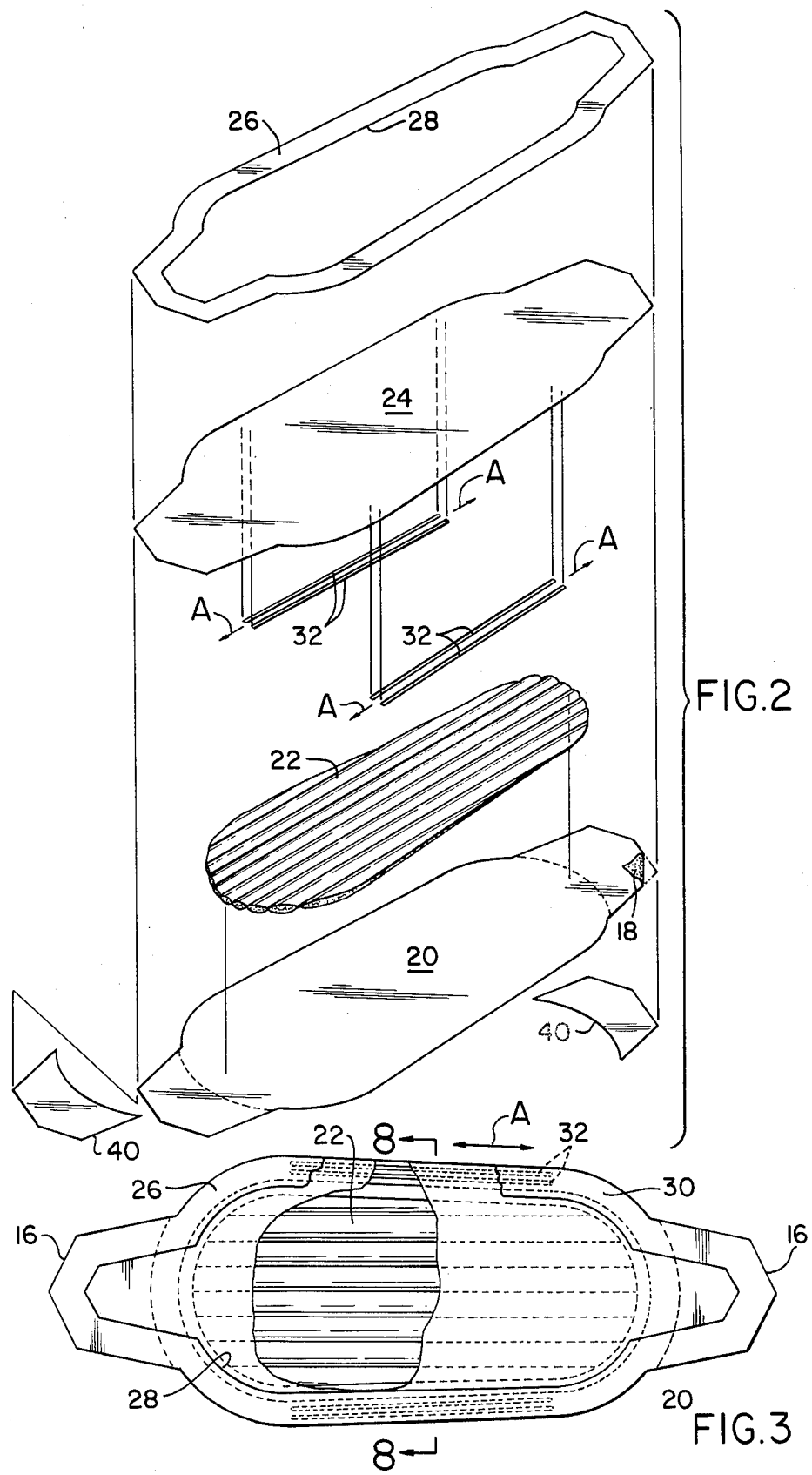

MENSTRUAL AND INCONTINENCE PAD

BACKGROUND OF THE INVENTION

The present invention relates to construction of sanitary napkins and in particular, to an improved menstrual pad and/or incontinence pad.

In my prior U.S. Pat. No. 4,421,512 dated Dec. 20, 1983 I disclosed a pantyhose garment having an integrally formed crotch support means for receiving a more or less conventional sanitary napkin in fluid tight confinement. A drawback of this construction lies in the fact that a specially constructed pantyhose, or undergarment must be used. While effective for intended use, this construction of pantyhose is somewhat uncomfortable for normal wear and thus has very limited use. Further, since the advent of menstruation is frequently rapid and with surprise, the user is most often not wearing the special pantyhose nor does she have special pantyhose accessible to her.

It is therefore, the primary object of the present invention to provide a sanitary napkin which can be worn with ordinary panties, pantyhose or similar undergarments, but which has the fluid tight confinement which was the hallmark of my prior patent.

Broadly, it is an object of the present invention to provide a self-contained, individual, independent sanitary napkin which can be used in combination with ordinary undergarments which provide both comfort and effective fluid absorbtion and confinement.

The foregoing objects, together with other objects and numerous advantages will be apparent from the following disclosure.

SUMMARY OF THE INVENTION

According to the present invention, a sanitary napkin is provided comprising a substantially oblong body formed of a plurality of vertically stacked layers comprising an underply of fluid impervious material, an intermediate ply of absorbent material, an upperply of highly fluid previous material and a peripheral binding ply of fluid impervious material having an inner and outer peripheral edge and defining a central opening into the body. The plies are adhered together about their outer peripheral edge and include an elastomeric member along each of the longitudinal side edges of the body, which resiliently contracts the body in the longitudinal direction drawing the body into a cup shape providing a deep compartment for retaining fluid between the underply and the intermediate ply and at the same time, raising the inner peripheral edge of the binding ply to form a continuous encircling wall against the flow of fluid from the compartment.

Preferably the intermediate ply of absorbent material is stitched or adhered along uniformly spaced parallel lines so as to provide in cross-section a corrugated effect from which separate chambers are formed between the intermediate ply and the underply, which minimize lateral flow of fluid.

Further, the body is provided with tabs at its front and rear end which may be provided with an adhesive allowing the sanitary napkin to be removably secured to a conventional panty or other undergarment with which it is used.

Still further, the oblong shape of the body can be modified so that one end is larger than the other. The larger end may be used for example, by an incontinent male while the smaller end may be used by a menstruating female.

Full details of the present invention are set forth in the following description and illustrated in the accompanying drawings.

BRIEF DESCRIPTION OF THE DRAWINGS

In the drawings

FIG. 1 is a perspective view of the sanitary napkin of the present invention placed for use within an undergarment of a wearer, FIG. 2 is an exploded view showing the components in isometric spaced relation, FIG. 3 is a top view of the sanitary napkin of the present invention, FIG. 4 is a side view of the sanitary napkin, FIG. 5 is a right end view of the sanitary napkin, FIG. 6 is an a plan view of the sanitary napkin during the manufacture thereof, FIG. 7 is a sectional view taken along line 7—7 of FIG. 6, FIG. 8 is a sectional view taken along line 8—8 of FIG. 2.

DESCRIPTION OF THE INVENTION

As seen in FIG. 1, the sanitary napkin of the present invention, generally depicted by the numeral 10 is applied by the wearer 12 on the inner crotch surface of a panty 14 or other conventional undergarment. To insure positioning of the sanitary napkin, the sanitary napkin is provided with a pair of longitudinally extending tabs 16 having an adhesive surface 18 capable of removably adhering to the fabric of the panty 14.

As seen in FIGS. 2 and 3, the sanitary napkin 10 comprises an underply 20 of impervious material, an intermediate ply of fluid absorbing material 22, an upperply 24 of highly pervious material such as gauze, net or the like and binding ply 26 of impervious material, preferably the same material as that which the underply 20 is formed of. The binding 26, provided with an inner peripheral edge 28 defines an opening through which fluids may pass inwardly into the sanitary napkin 10.

The plies 20, 22, 24 and 26 are sealed together, as seen in FIG. 3, along a continuous line 30 extending about the entire peripheral adjacent the outer edge thereof. Preferably, the peripheral seal 30 is created by a thread stitch or a heat seal (if the material permits) to bind the plies together and seal them so that leakage of fluid laterally through the plies is prevented. Set between the plies along the longitudinall side edges, are one or more elastomeric bands 32, which when applied during manufacture, are stretched (arrows A) so as to have an inherent contracting stress. The elastomeric bands 32 may be heat sealed sewn or otherwise adhered to one or more of the plies.

When relaxed, the elastomeric bands 32 contract forming a shirring 33 along each of the longitudinal side edges, thereby drawing in the longitudinal ends of the sanitary napkin toward each other, providing the conforming shape to the crotch of the wearer, as seen in FIGS. 4 and 6, in which in developed view, has a modified dumb-bell or figure eight shape, as a consequence of which the oblong shape of the sanitary napkin is modified such that one end 34 is slightly larger in the lateral direction than the other end 36. This allows the same sanitary napkin to be used both for females as a menstrual pad, (placing the smaller end 36 at the front of the torso) and by males as an incontinence pad, (placing the larger end 34 at the front of the torso).

The securing tabs 16 can be integrally formed with the underply 20 and allowed to extend in opposite longitudinal directions when the underply is stitched to the intermediate and upperplies 22, 24 as shown. The undersurface 38 of each tab 16, has applied to it a contact adhesive of conventional and readily available material covered by a removable protective sheet 40, which of course, is removed just prior to placement into the panty 14.

The elastomeric bands 30 can be replaced with a simple shirring thread which inherently gathers the material in much the same manner as the tensioned band 30. Other means may be used to gather the side edges under elastomeric bias.

The placement of the elastomeric band 30 in the positions indicated along the side edges of the sanitary napkin body 10, not only produces a simple curvarture to the sanitary napkin, but places the body under such stress that a deep cup 42 is formed having a well in its central portion, indicated generally by the reference numeral 44, as seen in FIG. 7. This well 44 produces a relatively deep reservoir for the collection of the fluid below the intermediate absorbent layer 22.

Furthermore, the elastomeric bands 30 place the binding ply 26 under such stress that its inner peripheral edge 28 stands upwardly away from the upper ply 24 forming a continuous peripheral wall 46 around the entire edge of the upper ply 24 preventing flow of fluid outwardly from the interior of the sanitary napkin.

To further control the flow of fluid, and prevent lateral flow both within the sanitary napkin and outwardly therefrom, the absorbent intermediate layer 22 is striated as by the use of a pluarlity of parallel seal lines 46 which convert the absorbent ply 22 into a corrugated cross-sectional form. The parallel seals 46 which extend longidudinally from end to end can be formed by heat sealing the material should a plastic resinous fiber be used to form the absorbent intermediate ply 22, or by simply stitching the same by a simple sewing measure. As a result of the formation of the corrugated cross-section, the reservoir 44 is further divided into a plurality of parallel small chambers which further isolate the fluid and resist lateral displacement.

While each ply is shown in the drawings and described as being of only a single thickness, it will be quite obvious that they may be formed of one or more layers.

It will be apparent that an improved sanitary napkin is thus produced, which while capable of retaining the fluid for an extended period, also isolates the fluid from the skin surface of the user. A particular advantage, arising from the parallel disposed elastomeric bands, lies not only in shaping the sanitary napkin, but in creating a deep fluid well and in addition, with the cooperation of the elastomeric bands and the peripheral binding, in creating a continuous circumferential wall to further insure effective retention of fluid.

Various modifications and changes have been suggested herein and others will be obvious to the reader. It is intended, therefore, that the present disclosure be taken as illustrative only and not limiting of the present invention.

What is claimed is:

1. A sanitary napkin having a substantially oblong body formed of a plurality of vertically stacked layers comprising an underply of fluid impervious material, an intermediate ply of absorbent material, an upperply of highly fluid pervious material, said intermediate ply being secured along uniformly spaced parallel lines so as to provide, in cross-section, a corrugated effect from which separate chambers are formed between the intermediate ply and said underply to minimize lateral flow of fluid, and a peripheral binding ply of fluid impervious material having an inner and outer peripheral edge and defining a central opening into the body, the body having one end larger than the other in the lateral direction such that, in plan view, the body generally resembles a figure eight configuration, said underply integrally formed with two planar projections one of which extends from the front edge of the last-mentioned ply and the other of which extends from the rear edge of such ply thus to define forward facing and rearward facing planar tabs that are aligned along the longitudinal axis of the body, each of said tabs including pressure sensitive adhesive means detachably to secure the same to an undergarment, said adhesive means including a removable protective cover, said plies being secured together about their outer peripheral edge and including an elastomeric member along each of the longitdudinal side edges of the body, which resiliently contracts the body in the longitudinal direction drawing the body in to a cup shape providing a deep compartment for retaining fluid between said underply and said intermediate ply and at the same time, raising the inner peripheral edge of said binding ply to form a continuous encircling wall against the flow of fluid from the compartment.

* * * * *